(12) United States Patent
Martiska et al.

(10) Patent No.: US 8,438,914 B2
(45) Date of Patent: May 14, 2013

(54) APPARATUS FOR MEASURING THE UNCONFINED YIELD STRENGTH AND TIME UNCONFINED YIELD STRENGTH OF BULK GRANULAR MATERIAL

(76) Inventors: Gregory P. Martiska, Newtown, CT (US); Paula Lamb Martiska, Newtown, CT (US)

(*) Notice: Subject to any disclaimer, the term of this patent is extended or adjusted under 35 U.S.C. 154(b) by 283 days.

(21) Appl. No.: 12/945,840

(22) Filed: Nov. 13, 2010

(65) Prior Publication Data

US 2012/0118072 A1   May 17, 2012

(51) Int. Cl.
 *G01N 3/08* (2006.01)
(52) U.S. Cl.
 USPC .......... 73/84; 73/87; 73/788; 73/790; 73/818; 73/821
(58) Field of Classification Search ................. 73/84, 87, 73/784, 788, 790, 799, 803, 818, 821, 825
 See application file for complete search history.

(56) References Cited

U.S. PATENT DOCUMENTS

| | | | | |
|---|---|---|---|---|
| 2,633,027 A * | 3/1953 | Bunnell | ........................... | 73/866 |
| 3,116,633 A * | 1/1964 | Cohron | ........................... | 73/784 |
| 3,443,423 A * | 5/1969 | Ma | ..................... | 73/84 |
| 3,457,777 A * | 7/1969 | Nielsen | ........................ | 73/84 |
| 3,478,572 A * | 11/1969 | Wislocki et al. | .................... | 73/9 |
| 3,616,685 A * | 11/1971 | Strom | ........................... | 73/84 |
| 3,820,385 A * | 6/1974 | Cordoba | ........................... | 73/84 |
| 3,939,701 A | 2/1976 | Peschl | | |
| 3,986,566 A * | 10/1976 | Hamilton | ........................ | 173/31 |
| 3,998,090 A * | 12/1976 | Wislocki | ..................... | 73/12.12 |
| 4,168,620 A * | 9/1979 | Schrader | ..................... | 73/12.09 |
| 4,784,206 A * | 11/1988 | Sauerman et al. | ............... | 164/18 |
| 4,794,799 A * | 1/1989 | Paakkinen | ..................... | 73/803 |
| 4,972,719 A * | 11/1990 | Vinson et al. | ................... | 73/790 |
| 5,275,056 A * | 1/1994 | Hamilton et al. | ............... | 73/794 |
| 5,289,728 A * | 3/1994 | Johanson et al. | ............... | 73/866 |
| 5,323,655 A * | 6/1994 | Eagan et al. | .................. | 73/432.1 |
| 5,824,913 A * | 10/1998 | Pyle | ................. | 73/818 |
| 5,911,164 A * | 6/1999 | McRae | ........................ | 73/815 |
| 6,026,692 A * | 2/2000 | Brovold | ........................ | 73/818 |
| 6,205,864 B1 * | 3/2001 | Vialletel et al. | ................. | 73/824 |
| 6,729,189 B2 * | 5/2004 | Paakkinen | ..................... | 73/824 |
| 6,769,317 B1 * | 8/2004 | Hamilton et al. | .......... | 73/864.44 |

(Continued)

OTHER PUBLICATIONS

Rock et al., "Investigations on the Caking Behaviour of Bulk Solids—Macroscale Experiements", Powder Technology, vol. 157, Jun. 2005.*

(Continued)

*Primary Examiner* — David Rogers

(57) ABSTRACT

An apparatus is provided for measuring the unconfined yield strength and time unconfined yield strength of bulk granular materials and powders. A sample of bulk material is consolidated under controlled pressure in a sample cup with a hole or holes in the bottom. A moveable base smaller than the internal cup dimensions covers the hole(s) to prevent material from escaping the cup and to provide a base for removing the consolidated sample from the cup. After a predetermined time, the consolidated sample is removed from the cup by lifting the base relative to the cup walls through the hole(s) in the bottom of the cup. Once removed from the cup, the strength of the consolidated sample is measured by applying pressure to the top of the sample until the sample breaks. For time tests, the sample is consolidate with weights over predetermined time periods.

3 Claims, 3 Drawing Sheets

U.S. PATENT DOCUMENTS

| | | | |
|---|---|---|---|
| 6,868,738 B2 * | 3/2005 | Moscrip et al. | 73/818 |
| 6,912,903 B2 * | 7/2005 | Hamblen et al. | 73/573 |
| 7,143,653 B2 * | 12/2006 | Abdel-Hadi et al. | 73/819 |
| 7,296,475 B2 * | 11/2007 | Conner | 73/754 |
| 7,549,315 B2 * | 6/2009 | Bulled et al. | 73/11.01 |
| 8,082,801 B2 * | 12/2011 | Caulfield et al. | 73/824 |
| 8,234,912 B2 * | 8/2012 | Suarez-Rivera et al. | 73/81 |
| 2005/0022608 A1 * | 2/2005 | Moscrip | 73/818 |
| 2008/0060444 A1 * | 3/2008 | Conway et al. | 73/821 |
| 2010/0005898 A1 * | 1/2010 | Regimand et al. | 73/803 |
| 2011/0214506 A1 * | 9/2011 | Khoury et al. | 73/784 |

OTHER PUBLICATIONS

Nysaeter et al., "Effects of Cyclic Loading and Various Test Conditions in an Uniaxial Tester", Particle and Particle Systems Characterization, No. 24, Nov. 2007.*

* cited by examiner

APPARATUS FOR MEASURING THE UNCONFINED YIELD STRENGTH AND TIME UNCONFINED YIELD STRENGTH OF BULK GRANULAR MATERIAL

CROSS-REFERENCE TO RELATED APPLICATIONS

Not Applicable

BACKGROUND OF THE INVENTION

1) Field of the Invention

This invention relates to an apparatus for measuring the unconfined yield strength of bulk granular materials and how it changes over time under different environmental conditions. The information produced by these measurements can determine how well a powder performs in various processes and equipment such as pharmaceutical tableting machines, pneumatics conveyors, container filling machines, drying systems, and catalyst towers.

2) Description of the Related Art

Many apparatus have been disclosed and produced that measure the unconfined yield strength of bulk granular materials. These systems range from simple cylindrical compaction cells to sophisticated shear testers and so called flow-no flow testers. The basic idea of the apparatus is to compress bulk granular material with a known pressure and then break the material to determine the strength it gained due to the compression. The known pressure is applied for a short time or over a long period to determine the time dependance of the strength measurement.

A typical apparatus for measuring unconfined yield strength is disclosed by Michael Rock and Jorg Schwedes in Powder Volume 157, June 2005. In the disclosed system, bulk material is compressed in a cylindrical mold that has been divided into two halves. During the compression, the two halves are held together by ring bands. After compression, the mold is removed and the freestanding material is broken by applying for to its top area. The main disadvantage of this approach is that sides of the mold must be manually removed to free the sample for the break test. In addition, the bottom of the mold must be blocked with a plug or flat plate to ensure sample does to flow from the bottom of the mold.

Another typical apparatus for measuring unconfined yield strength is disclosed by Trude Nysaeter and Gisle Enstad in Particle and Particle Systems Characterization Volume 24, June 2007. In the disclosed system, bulk material is compressed in a cylindrical mold. After compression, the mold is removed by holding the top of the sample in place and lifting the mold upward. The disadvantage of this approach is that the mold must be lifted up off of the sample slowly and carefully so the sample is not disturbed while force is maintained on the top of the sample to keep the sample in place.

Another apparatus for measuring unconfined yield strength is disclosed in U.S. Pat. No. 5,289,728. In the disclosed system, a sample of bulk material is compressed in a cylindrical mold with an opening at the bottom. During compression, the opening is blocked by a plug. After the sample has been compressed, the plug is removed and the sample is pushed through the bottom opening by pressure from above. The force required to push the sample from the mold is related to its unconfined yield strength. The disadvantage of this approach is that is expensive to automate and does not directly measure the unconfined yield strength of the sample.

Another typical apparatus for measuring unconfined yield strength is disclosed in U.S. Pat. No. 3,939,701. In the disclosed system, bulk granular material is loaded into cylindrical cavities and pressure is applied to the top of the cylinder to compress the powder. The cylinders are then rotated relative to each other and the resulting shear stress in the sample is measured. From this procedure the unconfined yield strength is calculated.

All of the disclosed apparatus for measuring unconfined yield strength suffer from one of the following problems, either they require a great deal of manual intervention or are complicated and expensive to automate and produce.

BRIEF SUMMARY OF THE INVENTION

After working on powder shear testers for some years, the inventors of the present invention determined that industry and academia needed a simple, easy to understand, and inexpensive apparatus to measure the unconfined yield strength. The apparatus also needed to have inexpensive test cells so that many samples could be prepared and put under pressure for various lengths of time and under different environmental conditions.

The heart of the invention is a test cell made up of a sample cup with a hole or holes in the bottom smaller than the internal dimensions of the cup. Fitting into the cup is a base that covers the bottom of the cup and hole(s). The cup can have inner walls perpendicular to the horizontal axis of the cup or angled walls so that the inner dimensions of the cup become smaller as the depth in the cup increases. The bulk granular material to be tested is then poured into the cup on top of the base and the cup is filled. After filling, a lid is placed on the cup and pressure is applied to compress the sample. This pressure is applied mechanically or with weights over a predetermined time period.

After compression, the compressed sample is removed from the sample cup by pushing the sample out of the cup from below through the bottom hole(s). The sample is then broken to determine the unconfined yield strength of the sample by applying pressure to the sample cup lid on top of the sample.

DETAILED DESCRIPTION OF THE INVENTION

Figure 1:
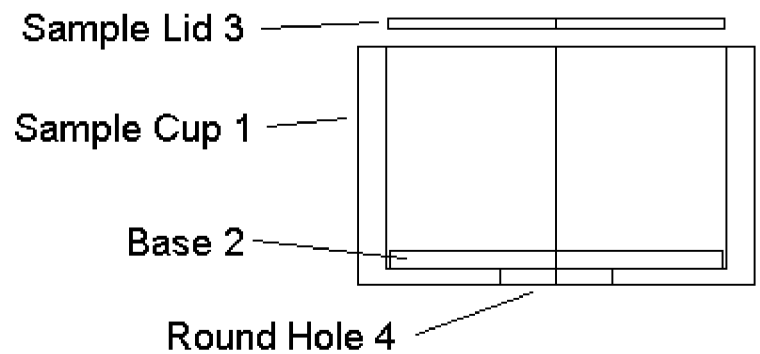
FIG. 1 presents a drawing of the preferred embodiment of the sample cup.
Figure 2:
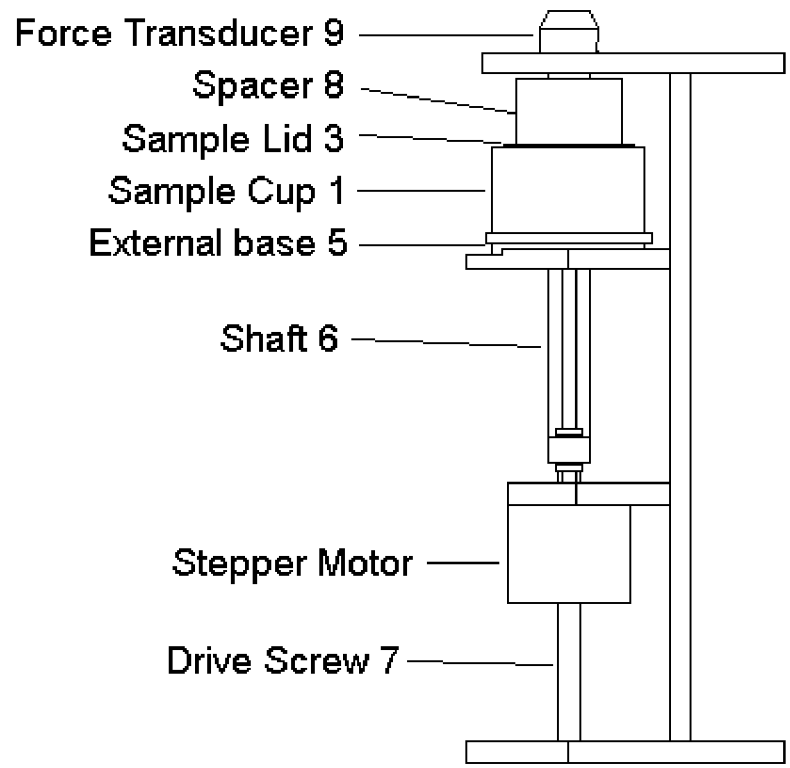
FIG. 2 presents a drawing of the preferred embodiment of the apparatus configured to apply pressure to the sample to compress it.
Figure 3:
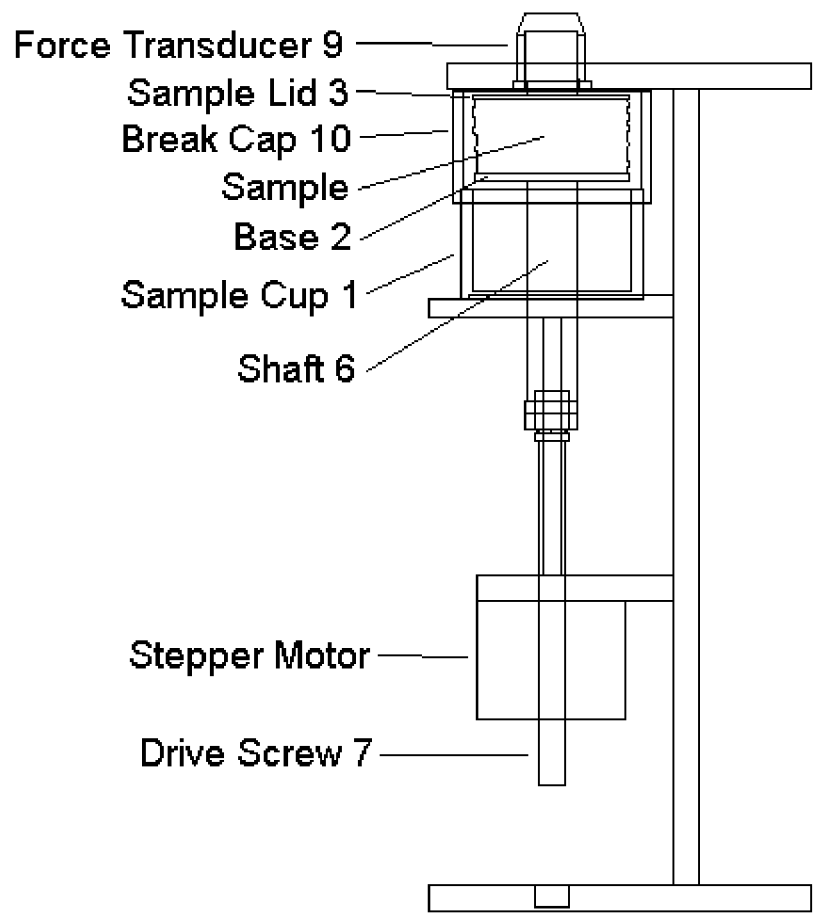
FIG. 3 presents a drawing of the preferred embodiment of the apparatus configured to remove the sample from the test cup and break it.
Figure 4:
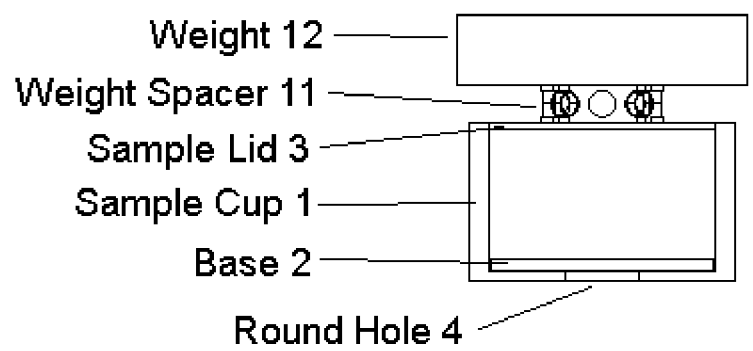
FIG. 4 presents a drawing of the preferred embodiment of the sample cup with consolidating pressure applied by weights.

The preferred embodiment of the invention is shown in FIGS. 2 and 3 . The test cell made up of a sample cup with a hole or holes in the bottom smaller than the internal dimensions of the cup. The preferred sample cup 1 is illustrated in FIGS. 1, 2 and 3 and is cylindrical with a round hole 4 in its center roughly one quarter of inner diameter of the cup. Fitting into the cup is a base that covers the bottom of the cup and hole(s). In the preferred cup, the base 2 is a flat disc with dimensions just smaller than the inner diameter of the cup to allow free movement. The bulk material to be tested is then poured into the cup on top of the base and the cup is filled. After filling a lid is placed on the cup and pressure is applied to compress the sample. In the preferred embodiment of the invention, pressure is applied to the sample lid 3 by lifting the sample cup on an external base 5 from below by a shaft 6 driven by a stepper motor driven screw 7 into a spacer 8 in contact with a force transducer 9.

After compression, the compressed sample is removed from the sample cup by pushing the sample out of the cup from below through the bottom hole(s). In the preferred embodiment of the invention, the external base 5 is removed from below the cell and a break cap 10 is put on top of the sample cup. The break cap has a notch for the sample cup and keeps the sample cup in place while the shaft 6 moves up and lifts the sample out of the cup through the hole 4 in the sample cup.

After the sample has been removed from the cup, the sample is then broken by applying pressure to the cup lid sitting on the sample. In the preferred embodiment of the invention, shaft 6 continues to lift the sample and push the cup lid 3 into the force transducer 9 until the pressure on the lid breaks the sample. The maximum pressure is recorded and used to calculate the unconfined yield strength.

To measure time unconfined yield strength, a weight spacer and weights are placed on the sample cup lid to apply the compression pressure to the sample. In the preferred embodiment of the invention, a cylindrical weight spacer 11 and cylindrical weights 12 are placed on the sample cup lid 3 to apply pressure to the sample. The sample cup with sample and weights can then sit for hours or days under controlled conditions to time consolidate the sample. The sample is then removed from the sample cup and broken to measure the change in unconfined yield strength over time.

Figure 5:
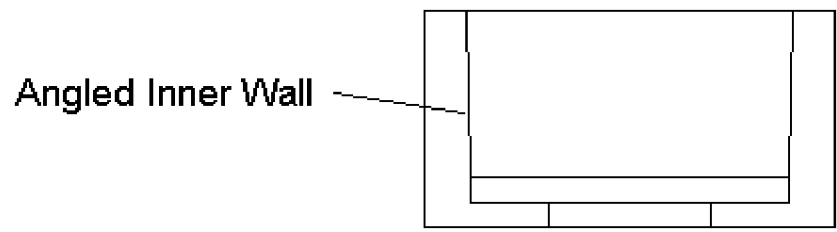
FIG. 5 presents an alternative embodiment of the sample cup with internal side walls at an angle relative to the vertical axis of the cup.

In another embodiment of the invention presented in FIG. 5, the internal sides of the sample cup are not perpendicular to the horizontal axis of the cup but rather are angled relative to the horizontal axis so that the inner dimensions of the sample cup become smaller as the depth of the cup increases. This greatly reduces the distance that the sample must to travel before it loses contact with the side walls of the sample cup. This reduces the chances of the sample being effected by the friction at the walls of the sample cup while it is being lifted from the sample cup.

What is claimed is:

1. An apparatus for testing the yield strength of granular materials and powders comprising:
   (a) a sample cup to hold a sample of a granular material or powder to be tested, the sample cup comprising:
      (i) a cup with an upper opening and one or more holes in its bottom, the one or more holes having an area dimension smaller than the inner area dimension of the bottom of the cup;
      (ii) a flat base that fits inside the cup and is supported by the bottom of the cup with dimensions large enough to prevent the sample material from falling through the hole(s) but small enough exit the top of the cup and to allow free movement in the cup;
   b) a drive mechanism to lift the sample from the sample cup through the upper opening so that the sample is unconfined and then drive the unconfined sample into a force transducer until the unconfined sample yields.

2. Testing apparatus according to claim 1 where the drive mechanism comprises a shaft attached to a motor driven screw that causes the shaft to pass through a bottom hole in the sample cup and lift the sample from the sample cup through the upper opening.

3. Testing apparatus according to claim 1 where the sample cup includes a lid with dimensions smaller than the upper opening of the sample cup for applying pressure to the sample in the cup and to apply pressure to the sample after it has been lifted from the cup.

\* \* \* \* \*